United States Patent [19]

Keller et al.

[11] Patent Number: 5,071,973
[45] Date of Patent: Dec. 10, 1991

[54] PROCESS FOR PREPARING OF NON-THROMBOGENIC SUBSTRATES

[76] Inventors: Ruprecht Keller, Schurzelterstrasse 206; Hanno Baumann, Augustinerweg 23, both of D-5100 Aachen, Fed. Rep. of Germany

[21] Appl. No.: 590,527

[22] Filed: Sep. 27, 1990

Related U.S. Application Data

[63] Continuation of Ser. No. 119,633, Nov. 12, 1987, abandoned.

[30] Foreign Application Priority Data

Nov. 20, 1986 [DE] Fed. Rep. of Germany ....... 3639561

[51] Int. Cl.$^5$ .................... A61K 31/715; A61K 37/02
[52] U.S. Cl. .......................................... 536/8; 514/54; 514/56; 530/395; 424/486; 424/488; 536/4.1; 536/123; 536/124; 523/112
[58] Field of Search ............... 514/8, 54, 56; 530/395; 424/101, 486, 488; 536/4.1, 123, 124; 523/112

[56] References Cited

U.S. PATENT DOCUMENTS

| | | |
|---|---|---|
| 3,518,243 | 6/1970 | Butti et al. ............... 530/395 |
| 3,607,650 | 9/1971 | Bertellini et al. ............ 530/395 |
| 3,673,612 | 7/1972 | Merrill et al. ............... 514/56 |
| 4,217,339 | 8/1980 | Bohn et al. ................. 530/395 |
| 4,219,520 | 8/1980 | Kline ........................ 514/56 |
| 4,230,699 | 10/1980 | Fussi et al. ................ 514/54 |
| 4,239,664 | 12/1980 | Teng et al. ................. 514/56 |
| 4,265,927 | 5/1981 | Ericksson et al. ............ 514/56 |
| 4,326,532 | 4/1982 | Hammar ..................... 514/56 |
| 4,415,490 | 11/1983 | Joh .......................... 514/56 |
| 4,438,108 | 3/1984 | Sanders et al. .............. 536/123 |
| 4,460,694 | 7/1984 | Fletcher .................... 530/395 |
| 4,634,762 | 1/1987 | Feijen et al. ............... 530/350 |
| 4,676,975 | 6/1987 | McGary et al. ............... 514/56 |
| 4,713,402 | 12/1987 | Solomon ..................... 514/54 |
| 4,748,156 | 5/1988 | Aoki et al. ................. 514/8 |
| 4,755,379 | 7/1988 | Jozefonvicz et al. .......... 514/56 |
| 4,806,595 | 2/1989 | Noishiki et al. ............. 514/56 |
| 4,810,586 | 3/1989 | Halpern et al. .............. 536/1.1 |
| 4,820,689 | 4/1989 | Ikuzawa et al. .............. 514/8 |

FOREIGN PATENT DOCUMENTS

| | | |
|---|---|---|
| 0066908 | 12/1982 | European Pat. Off. ........... 514/54 |
| 0136916 | 4/1985 | European Pat. Off. ........... 514/56 |
| 2610698 | 9/1976 | Fed. Rep. of Germany ........ 514/56 |
| 3511199 | 10/1986 | Fed. Rep. of Germany ........ 530/395 |
| 49-38945 | 4/1974 | Japan ........................ 514/54 |
| 1249907 | 10/1971 | United Kingdom .............. 530/395 |

OTHER PUBLICATIONS

*Immobilised Cells and Enzymes: A Practical Approach*, by J. Woodward, (1985).
*Methods in Enzymology*, "Immobilized Enzymes", vol. XLIV, (1976) by K. Mosbach, pp. 11, 15, 47, 149 and 177.
*Physical Chemistry*, fourth edition, by W. Moore (1962), p. 550 and chapter 13, section 3.

Primary Examiner—Ronald W. Griffin
Assistant Examiner—Nancy S. Carson
Attorney, Agent, or Firm—Collard, Roe & Galgano

[57] ABSTRACT

The present invention refers to a method concerning the preparation of hemo-compatible substrates by incorporation, adhesion and/or modification and embodiment of non-thrombogenic endothelial cell surface polysaccharide (HS I) in its peptide-bound or free form on and/or mixed with synthetic and biopolymers (Substrates) by way of physical distribution, adhesion to the surface and/or chemical embodiment, which can be used in medicine as blood-compatible substrates. These polymers can be presented in form of fibres, hollow fibres, membranes, organ spare parts, canulas, syringes, tubes, blood containers, or in other forms, or they can be prepared from other material.

15 Claims, No Drawings

PROCESS FOR PREPARING OF NON-THROMBOGENIC SUBSTRATES

This is a continuation of copending application Ser. No. 07/119,633 filed on Nov. 12, 1987, abandoned.

The present invention refers to a method concerning the preparation of hemo-compatible substrates by incorporation, adhesion and/or modification and anchoring of non-thrombogenic endothelial cell surface polysaccharide (HS I) in its peptide-bound form or in its free form on or into synthetic and biopolymers (Substrates) by way of physical distribution, adhesion to the surface and/or chemical anchoring. These hemo-compatible substrate can be used in medicine as blood-compatible substrates. These polymers can have the form of fibres, hollow fibres, membranes, organ spare parts, canulas, syringes, tubes, blood containers, or can have other forms, or they can be prepared from other material.

It is known that non-physiological polymers more or less rapidly cause the coagulation of blood if no additional remedial measure is supplied. In addition to that it is known that the flow relations of blood, which are inter alia influenced by the form, the surface conditions and the elastic nature of the substrates, also influence the coagulation process of blood. If, however, suitable polymers, such as EP-copolymers, cellulose, fluorinated polyethylene, polyether urethane, polyether carbonate, hydrogels of e.g. polyacrylamide, are chosen the coagulation of blood after contact with the polymer is significantly reduced.

Another way for reducing the coagulation of blood to a greater extent is to cover hydrophobe polymers with albumin. One more possibility for the reduction of the blood coagulation is the application of sulfonated or sulfated products, such as sulfated polystyrene or copolymers that contain vinylsulfonic acid. The best anticoagulant effects have been achieved by the introduction or surface modification of polymers with anticoagulant substances, such as heparin or heparinoids. Inclusion of heparin into microporous plastic materials, from which it can easily diffuse out, already leads to an anticoagulant effect. Better effects have been achieved by surface modification of styrene for example and subsequent salt-like binding of heparin. The materials that were produced thus far could not provide a blood-compatibility, which corresponds e.g. to the intact endothelial cell surface on the luminal side of the blood vessel.

The task of the present invention is to provide a method for the preparation of hemo-compatible polymer substrates.

The subject of the present invention is a method for incorporation, adsorption or binding of a biological inert endothelial cell surface polysaccharide, which is especially inert against coagulation, in its free or peptide-bound form on or into suitable polymers. This incorporation, adsorption or binding can be achieved by way of Van der Waals interactions, salt bridges, chelation, or covalent bonds. The blood-compatibility of such modified polymers is clearly improved in contrast to all polymers that are known until now.

The polymers, modified in the above described way, can be utilized in artificial organs, membranes, hollow fibres, oxigenators, syringes, tubes, containers, fibre-containing materials, which are characterized in a way that:

1. HS I is incorporated or immobilized or embodied on the surface of synthetic and biopolymers according to the known methods of immobilization of enzymes, the preparation of membranes, the plastic processing and the methods of polymer chemistry by means of Van der Waals forces, hydrophobic interactions, chelations and salt like bonds.

2. HS I is covalently embodied in synthetic polymers and biopolymers according to the methods of the chemistry of peptides, proteins, sugar and polymers.

The term HS I is to be understood as an endothelial cell surface proteo polysaccharide that has a molecular weight of about 195,000 and whose polysaccharide part has a molecular weight of 35,000 for 3-4 polysaccharide chains per molecule, corresponding to a peptide part of 55,000. The polysaccharide part, a subunit of the molecule, which is accessible by means of proteolysis or alkali degradation, is shown to be completely inert in all biological aggregation and operational tests, e.g. with reference to

- interactions with the coagulation factors
- the interaction with antithrombin III
- interactions with heparin binding growth factors, such as platelet derived growth factors, EGF etc.
- interactions with structural polymers of the connective tissue, such as collagen I-VI, laminin, fibronectin, nidogen, and entactin
- interactions with thrombocytes.

This substance can be used as polysaccharide component with or without the remaining peptide component for the binding to polymers in order to prepare hemo-compatible substrates. The long-time blood-compatibility of peptide-bound HS I polysaooharide can be reduced by means of binding of plasma proteins to the remaining peptide component or by means of immunization when using HS I from other species. In such a case the peptide component is either shortened by way of a further proteolysis or, if it is required, completely removed by the action of 0.5M NaOH.

HS I is isolated according to its molecular weight, its hydrophobicity and its charge from the conditioned medium of mass cultured endothelial cells or from the endothelial cells themselves:

Bovine aortic endothelial cells or endothelial cells from other species and other tissues, such as cornea, liquor cavities etc. are separated from the tissue through treatment with collagenase, through mechanical relief, through treatment with other reagents such as heparinase and/or heparitinase, through treatment with trypsin or other proteases, through action of EDTA, EGTA or other chelating agents, and then cultured in great numbers in conventional tissue culture bottles, in Petri dishes, in hollow fibre perfusion cultures, on beads, in cylindrical bottles or in different manners ($2 \times 10^9$ cells/preparation). The culturing takes place according to the conventional methods of tissue and cell cultures.

The cells are removed in the described manner, homogenized by way of repeated freezing and thawing, ultrasonics treatment, treatment in a potter or in different manners, centrifuged at $10,000 \times g$ and the supernatant is dissolved with detergents, preferably 2% SDS.

The conditioned medium of the endothelial cells can be used as another source of HS I. For this purpose the medium is first incubated with chondroitinase ABC in the presence of chelating agents, such as EDTA, evaporated in a rotary evaporator, and then worked up in principally the same manner as is described for the material of cellular origin;

The materials that contain HS I are chromatographed on Sepharose CL-4B. The used dimensions of the columns have diameter to height ratios from 1:10 to 1:50 (e.g. 10×200 cm). The eluate can be 0.13M Tris/HCl, 0.1% SDS pH 7.4 or any other suitable elution compound. The detection of HS I during the qualitative step can be done by reactions of aliquots, which are taken from the chromatography fractions, in form of detection methods for sugar, e.g. the orcin reaction, detection methods for uronic acids, e.g. the carbazole reaction, in form of an addition of a small portion of radioactive labelled HS I before Sepharose chromatography or in a different manner.

The thus identified chromatography fractions that contain HS I are evaporated in a ratio of 1:10 with the help of the rotation evaporator, desalted through chromatography on Sephadex G-25, dialysis, ultrafiltration on ultrafiltration membranes, precipitated in 80% ethanol, or in different manners, and is then absorbed in 3-7M urea, in detergents, such as 0.1% Triton X-100, and in buffer salts, such as 0.1M NaAc pH 6.5. The solution is applied to an anion exchange column, such as DEAE-cellulose in the presence of 7M urea, detergents and buffer salts and afterwards eluted from the column with a salt gradient (e.g. 0-1M NaCl).

The following methods can be used for a further purification:
- density ultracentrifugation in a CsCl-gradient at a medium concentration of 1.4 g/ml preferably
- further cycles of gel-chromatography/ion exchange chromatography
- chromatography on lipophilic gels, such as Octyl-Sepharose
- HPLC on ion exchange columns, silica gel columns, reversed phase columns and gel columns.

The following criteria are used for testing of the homogeneity of a HS I preparation:
1. non-detectability of galactosamine in the hydrolysate shows the freedom of contaminating chondroitin sulfate
2. an absorption maximum at 280 nm and a minimum at 260 nm show the freedom of contaminating RNA or DNA
3. one band in NU-Sieve-agarose gel electrophoresis and one band in SDS gel electrophoresis show the absence of contaminating proteins
4. after the incubation with 0.5M NaOH for 12 h at 4° C. a high-molecular polysaccharide is found.

Modifications of the preparation make it possible to liberate the HS I polysaccharide or peptido polysaccharide by alkali degradation (e.g. incubation into 0.5M NaOH for 12 h at 4° C.) or proteolytic degradation (e.g. with papain or pronase) or other methods during each single step of the preparation, also from untreated cells or from the untreated medium, and it can be purified by gel chromatography, ion exchange chromatography, density gradient ultracentrifugation, HPLC on gel permeation columns, on silica gels and/or reversed phase columns. With the exception of point 3, mentioned above, all of the described homogeneity criteria are used for such a preparation.

The term "synthetic polymers and biopolymers" is to be understood as all known natural polymers and all synthetic polymers, prepared up to now that are seen as homo- and different copolymers with varying tacticity, varying molecular weight, varying sequence order of the particles with statistical and/or alternating sequence; block copolymers with varying distribution of the sequence lengths, triblock copolymers, ionomers, graft copolymers, polymers with a varying degree of cross linkage, as well as polymers that are modified by polymer analogous reactions. Those polymers that are listed in the following are according to the invention only a few examples of polymers that can be modified additionally by further copolymerizations, grafting or polymer analogous reactions, and thus form an enlarged choice of suitable synthetic and biopolymers:

Polyolefines, polyethylene (HDPE, LDPE, LLPE), fluorinated polyethylene, copolymers of ethylene with butene-(1), pentene-(1), hexene-(1), copolymers of ethylene and propylene, EPR-rubber or EPT-rubber (third component with diene structure, such as dicyclopentadiene, ethylidene norbonene, methylene endomethyl hexahydro naphthalene, cis-cis-cyclooctadiene-1,5, hexadiene-1,4), hexyne (1-hexene methyl hexadiene); ethylene-vinyl acetate-copolymer, ethylene-methacrylic acid-copolymer, ethylene N-vinyl carbazole, ethylene trifluoromonochloroethylene, polypropylene, polybutene-(1), poly-4-(methyl pentene-(1)), polyisobutene copolymer, isobutene-styrene-copolymer, butyl rubber, polystyrene and modified styrene, chloromethylated styrene, sulfonated styrene, poly-(4-amino styrene), styrene-acrylonitrile-copolymer, styrene-acrylonitrile-butadiene-copolymer, acrylonitrile-styrene-acrylic ester-copolymer, styrene-butadiene-copolymer, styrene-divinyl benzene-copolymer, polydienes in cis-trans, in 1-2 and in 3-4 configuration, polybutadiene, polyisoprene, purified natural rubber, chloroprene, polystyrene, butadiene copolymer (SBR), triblock polymers (BBS), NBR-acrylonitrile-butadiene-copolymer, poly-(2,3-dimethyl butadiene), a tri-block copolymer of polybutadiene terminated with cycloaliphatic secondary amines or benzyl-L-glutamate or polypeptides or N-carbobenzoxylysine, poly-(alkenamer)-polypentenamer, poly-(1-hexene methyl hexadiene), polyphenylenes, poly-(p-xylylene), polyvinyl acetate, vinyl acetate-vinyl stearate-copolymer, vinyl acetate-vinyl pivalate-copolymer, polyvinyl alcohol, polyvinyl formal, polyvinyl butyral, polyvinyl ether, poly-(N-vinyl carbazol), poly-N-vinyl pyrrolidone, poly-(4-vinyl pyridine), poly-(2-vinyl pyridine oxide), poly-(2-methyl-5-vinyl pyridine), butadiene-(2-methyl-5-vinyl pyridine)-copolymer, polyethylene tetrafluoride, tetrafluoroethylene-hexafluoropropylene-copolymer, tetrafluoroethylene-perfluoropropylvinylether-copolymer, tetrafluoroethylene-ethylene-copolymer, tetrafluoroethylene-trifluoronitrosomethane-copolymer, ethylene tetrafluorideperfluoromethyl vinyl ether-copolymer, ethylene tetrafluoride-(perfluoro-4-cyanobutyl vinyl ether)-copolymer, poly-(trifluoromonochloroethylene), tri-fluoromonochloroethylene-ethylene-copolymer, polyvinylidene fluoride, hexafluoroisobutylene-vinylidene fluoride-copolymer, polyvinyl fluoride, polyvinyl chloride, impact-resistant PVC by addition of ABS, MBS, NBR, chlorinated PE, EVAC or poly-acrylates, soft PVC, post-chlorinated PVC, vinyl chloride-vinyl acetate-copolymer, vinyl chloride-propene-copolymer, polyvinylidene chloride, vinyl chloride-vinylidene chloride-copolymer, vinylidene chloride-acrylonitrile-copolymer, polyacrylic acid, acrylic acid-itaconic acid-copolymer, acrylic acid-methacrylic acid-copolymer, acrylic ester-acrylonitrile-copolymer, acrylic ester-2-chloroethyl vinyl ether-copolymer, poly-(1,1-dihydroperfluorobutyl acrylate), poly-(3-perfluoromethoxy-1,1-dihydroperfluorobutyl acrylate), polysulfone, polyacrolein polyacrylamide, acrylic acid-acrylamidecopolymer, acrylamide-maleic acid-copolymer, acrylamide-hydroxymethyl methacrylate-copolymer, acrylamide-methyl methacrylate-copolymer, acrylamidemethyl acrylate-copolymer, acrylamide-maleic anhydride-copolymer, acrylamide-methacrylic anhydride-copolymer, acrylamide-anilino acrylamide-copolymer, acrylamide-(N-acrylol-4-carboxy methyl-2,2'-dimethyl thiazoline)-copolymer, polymethacrylamide, methacrylic acid-methacrylonitrile-copolymer, methacrylic acid-3-fluorostyrene-copolymer, methacrylic acid-4-fluorostyrene-copolymer, methacrylic acid-3-fluoroanilide-copolymer, nitrated copolymers of methacrylic acid with methacrylic acid-3-fluoroanilide or fluorostyrene, or copolymers of methacrylic acid with 3,4-isothiocyanatostyrene, or N-vinylpyrrolidone with maleic anhydride, or polyvinyl alcohol and polyallyl alcohol, polyacrylonitrile, acrylonitrile-2-vinyl pyridine-copolymer, acrylonitrile-methallyl sulfonate-copolymer, acrylonitrile-N-vinyl pyrrolidone-copolymer, PAN containing hydroxyl groups, acrylonitrile-vinyl acetate-copolymer, acrylonitrile-acrylic ester-copolymer, polyallyl compounds, polydiallyl phthalate, polytris allyl cyanurate, poly-α-cyano-acrylates, polydimethyl aminoethyl methacrylate and copolymers with acrylonitrile, methylmethacrylate-lauryl methacrylate-copolymer, para-acetaminophenyl ethoxy methacrylate-methyl methacrylate-copolymer, glycol dimethacrylate-methacrylate-copolymer, poly-2-hydroxyethyl methacrylate, 2-hydroxy ethyl methacrylate-methyl methacrylate-copolymer, glycol methacrylate-glycol dimethyl methacrylate-copolymer, HEMA-styrene-block and graft copolymers, poly-N,N'-P,P'-oxy diphenylene mellite imide, polydiethylene glycol bisallyl carbonate, aliphatic polyethers, polyoxymethylene, polyoxyethylene, polyfluoral, polychloral, polyethylene oxide, polytetrahydrofuran, polypropylene oxide, ethylene oxide-propylene oxide-copolymer, propylene oxide-allyl glycidyl ether-copolymer, polyepichlorhydrin, ethylene oxide-epichlorhydrin-copolymer, poly-1,2-dichloromethyl-ethylene oxid, poly-2,2-bis-chloromethyl-oxa cyclobutane, epoxy resins, bisphenol -A-diglycidyl ether, phenol formaldehyde resin, kresol formaldehyde resins, cross linkage with carbon anhydrides, amines as diethylenediamine, isophorondiamide, 4,4'-diamino diphenyl methane, aromatic polyethers, polyphenylene oxides, polyphenol, phenoxy resins, aliphatic polyesters, polylactide, polyglycolide, poly-β-propionic acid, poly-β-D-hydroxy butyrate, polypivolactone, poly-ε-caprolactone, polyethylene glycol sebazate, polyethylene glycol adipate, unsaturated polyester from maleic anhydride, phthalic anhydride, isophthalic acid, terephthalic acid or HET acid with ethylene glycol, 1,2-propylene glycol, neopentyl glycol, oxyethylated bisphenols or cyclododecandiols, cross linkage of unsaturated polyester resins or vinylester resins by way of copolymerization of unsaturated polyesters with styrene, methylacrylate, vinyl monomers, vinyl acetate, methyl methacrylate, polycarbonate from bisphenol A and its derivatives and polyethers, segmented polycarbonates from bisphenol A and its derivatives, and aliphatic polyethers and aliphatic polyesters (see above), polyethylene glycol terephthalate (PET) surface modified, grafted with acrylic acid or by partial hydrolysis of the surface of PET, polybutylene glycol terephthalate, polyethylene glycol terephthalate, polyethylene glycol terephththalate-adipate, polyethylene glycol, terephthalate segmented with polyether blocks and aliphatic polyester blocks and polyhydrofuran blocks, poly-p-hydroxy benzoate, hydroxybenzoic acid-isophthalic acid-copolymer, hydroxybenzoic acid-hydroquinone-copolymer, hydroxybenzoic acid-terephthalic acid-copolymer, hydroxybenzoic acid-p,p'-diphenyl ether-copolymer, polyvinyl pyrrolidon, polyvinyl pyrrolidene-maleic anhydride-copolymer, alkyd resins of glycerin, trimethylpropane, pentaerythritol, sorbitol with phthalic acid, succinic acid, maleic acid, fumaric acid, adipic acid and fatty acids of linseed oil, castor oil, soyoil, coconut oil, aliphatic polysulfides —$(R—S_x—)x$=sulfur grade, aromatic polysulfides, polythio-1,4-phenylene, aromatic polysulfide ethers of phenol and thiophene, polyether sulfones, polysulfo-1,4 -phenylene, poly-p-phenylene sulfone, polyimines, polyethylene imine, branched polyethylene, imines, polyalkylene imines, polyamides, polyhexamethyleneadipic amide, polyhexamethylene sebacic amide, polyhexamethylene dodecane diamide, polytridecane brassylic amide, versamides from vegetable oils with diamines and triamines, polyamide of ω-aminocarboxylic acids with $α,β,γ,δ$-aminocarboxylic acids or lactams, terephthalic acid-m-aminobenzamide-copolymer, polyamide hydrazide, e.g. of isophthalic acid and m-aminobenzohydrazide, polypiperazine amide, e.g. of fumaric acid and dimethylpiperazine, polybenzimidazoles of terephthalic acid and tetramino benzene (substituted), or of diamino phenyl ethers and dichlorophenyl sulfone (substituted and cyclizated), or of m-phenylene isophthalimide and terephthalamide, polyimides, e.g. of pyromellitic dianhydride, methoxy-m-phenylene diamine, pyrrones, e.g. of pyromellitic dianhydride and diamino benzidine, aromatic polyamides, poly-m-phenylene isophthalamide, poly-p-benzamide, poly-p-phenylene terephthalamide, m-amino benzoic acid-p-phenylene diamine-isophthalic acid-copolymer, poly-4,4'-diphenyl sulfone terephthalamide from terephthalic acid and hexamethylenetetramie, terephthalic acid and trimethyl hexamethylenediamine and 2,4,4-trimethyl hexamethylenediamine, from terephthalic acid, diaminomethylene norbonene and caprolactam, from isophthalic acid and laurinlactam, from isophthalic acid and di-4-(cyclohexyl amino-3-methyl)-methane, from 1,12-decane diacide and 4,4'-diamine dicyclohexyl methane, aromatic polyamides with heterocycles, e.g. dicarboxylic acid dichloride, terephthalic acid and isophthalic acid, diaminic heterocycles with oxidazole, triazole, bithiazole and benzimidazole structures, 3-(p-aminophenyl)-7-amino-2,4-(1H,3H) -chinazolindion+isophthalic acid, polyaminoacids, poly-methyl-L-glutamat, poly-L-glutamic acid etc., copolypeptides, e.g. from glutamic acid and leucine, glutamic acid and phenylalanine, glutamic acid and valine, glutamic acid and alanine, lysine and leucine, p-nitro-D,L-phenylalanine and leucine etc., polyureas from diisocyanates with diamines and ureas, polyurethane from aliphatic and aromatic diisocyanates and bifunctional and trifunctional hydroxy containing polyesters (s. above) and aliphatic polyethers (s. above) and eventually modification with bifunctional amino group containing, hydroxyl group containing and carboxyl group containing materials, e.g. hexamethylene diisocyanate, diphenyl methane diisocyanate, toluylene diisocyanate 2,4 and 2,6, tolidine diisocyanate, xylylene diisocyanate, glycerin, ethylene glycol, pentaerythrite, 3-dimethylamino-1,2-propanediol and carbohydrates, aliphatic and aromatic dicarboxylic acids and their derivatives, o,m,p-phenylenediamine, benzidine, methylene-bis-o-chloroaniline, p,p'-diamino diphenylmethane, 1,2-diaminopropane, ethylene diamine, amino resins from urea and cyclic urea, melamine, thiourea, guanidine, urethane, cyanamide, acid amides and formaldehyde as well as longer aldehydes and ketones, silicones, polydialkylsiloxane, diaryl siloxane and alkyl-aryl siloxanes as dimethyl-, diethyl-, dipropyl-, diphenyl-, phenylmethyl siloxane, silicones containing functional groups, e.g. allyl groups, γ-substituted fluorosilicones containing amino groups and vinyl groups, e.g. aminopropyl triethoxysiloxane, 2-carboxyl propyl methyl siloxane, block polymer with dimethylsiloxane units and polystyrene or polycarbonate blocks, triblock copolymers of styrene, butyl acrylate with α,ω-dihydroxy-polymethylsiloxane, 3,3,3-trifluoro propyl methylsiloxane, avocane (90% polypropylene glycol and 10% siloxane), block copolymers of silicone and polycarbonate, cellulose and cellulose derivatives, e.g. acetylcellulose, perfluorobutyryl ethylcellulose, perfluoroacetylcellulose, cellulose nitrate, carboxy-methyl cellulose, regenerated cellulose, regenerated cellulose from viscose and similar cellulose derivatives, agarose, polysaccharides as carrageenan, dextran, mannane, fructosane, chitin, pectine, glycosamino glycanes, starch, glycogen, alginic acids, and all deoxypolysaccharides and halogeno-deoxypolysaccharides, aminodeoxypolysaccharides or sulfhydryl-deoxypolysaccharides and their derivatives, mureine, proteins, e.g. albumin, gelatin, collagene I–XII, keratin, fibrin and fibrinogen, casein, plasmaproteins, milk proteins, structure proteins from animal and plant tissue, soy proteins, proteins of the food industry.

The enlarged selection of polymers results from the fact that the above listed polymers, which are synthesized with varying monomers, are copolymerized with other so far known monomers (these are the monomers that are enlisted in the book *Functional Monomers*, Ed. R.H. Yocum and E.B. Nyquist, Vols. I and II, Marcel Dekker, New York 1974). In addition to that the above listed polymers can be modified partially or completely by way of grafting, polymer analogous reactions, synthesis of further block copolymers or graft copolymers. Polymer mixtures, alloys, coated polymers and polymers in the form of composite materials can also be synthesized. These polymers can be surface modified by way of high-energy radiation, illumination, oxidation, hydrolytic degradation, photochemical reactions, halogenation, sulfochlorination, chloromethylation, reaction with radical formers Na, Li, K in organic solvents etc.

Polymer derivatives can also be prepared with bi- and polyfunctional cross linking reagents that are known from the preparation of reactive polymers according to the methods of peptide, protein, polysaccharide and polymer chemistry. The following gives a selection of the functional groups or cross linking molecules that can be used to derivate polymers:

Phosgene, formaldehyde, glyoxal, acroleine, glutar dialdehyde, azides, activated esters, anhydrides, acid chlorides, esters, mixed anhydrides, bromocyanogen, difluoronitrobenzene, thioisocyanates, epoxyde, imide, isocyanate, urethione groups, diisocyanates, triisocyanates, maleinimide, dicyclohexyl carbodimide, N,N'-bis-(trimethyl silyl sulfur diimide), peroxides, vinylketo groups, aromatic diazo compounds, vinyl sulfone, trichlorotriazine, monochlorotriazine, dichlorotriazine, bromochlorotriamide, bromoacrylamide, difluoromonochloropyrimidine, trichloropyrimidine, dichlorochinoxaline, chloroacetylamino groups, chloroacetylurea, β-halogenopropionamide, α,β-dihalogenopropionamide, β-quarternary ammonium propionamide, β-sulfato propionamide, β-sulfonyl propionamide, substituted alkane dicarboxamides, substituted alkane monocarboxylates, substituted cycloalkane carboxamides, alkene monocarboxamides, arylamides, croton amides, substituted arylamides, mono-, di- and trihalogenoarylamides, substituted croton amides, alkene dicarboxamides, cyclic halogenomaleinimides, alkine carboxamides, substituted aliphatic ketones, amides of substituted aliphatic sulfonic acids, substituted methane sulfonamides, substituted ethane sulfonamides, β-sulfato ethyl sulfonamides, β-thiosulfato ethyl sulfonamides, quarternary ammonium ethane sulfonamide, vinyl sulfonamide, β-chlorovinyl sulfonamide, esters of reactive aliphatic sulfonic acids, β-substituted ethyl sulfones, β-thiosulfato ethyl sulfones, β-halogenovinyl sulfone, β-substituted ethylamine derivatives, β-sulfato ethylamine, β-halogenoethyl pyrrazolone, N-(β-halogenoethyl)-amides, N-(β-sulfatoethyl)-amides, β-substituted ethyl ammonium compounds, β-substituted ethylamides, N,β-halogenoethyl sulfonamides, β,γ-dihalogenopropionylamides of sulfonic acids, ethylenimine and ethylenimine compounds, allyl groups, propargyl groups, diallyl phthalate, triallyl cyanurate, benzyle derivatives, 2-substituted thiazole carboxylic acids, chlorosulfonyl pyridine, 4-substituted-3,5-dicyano-2,6-dichloropyridine, 2,6-bis-(methyl sulfonyl)-pyridine-4-carbonyl chloride, chloropyrazidine, dichloropyridazone, 1-alkyl-4,5-dichloro-6-pyridazone, chloro- and bromopyrimidine, 3-(2',4',5'-trichloropyrimidyl-(6'-amino)-aniline, 4,5,6-trichloropyrimidine-2-carbonyl chloride, trifluoropyrimidine, trifluoromonochloropyrimidine, 2-chlorotriazinyl derivatives, 2-chloro-4-alkyl-s-(triazinyl-6-aminocarboxylic acid), 2-chlorobenzothiazolcarbonyle, 6-amino-2-fluorobenzothiazol, 2-methylsulfonyl-6-aminobenzothiazol, 2,3-dichlorochinoxaline-6-carbonyl chloride, 1,4-dichlorophthalazine-6-carbonyl chloride, 3-chloro-1,2,4-benzotriazin-1-N-oxide-7-carbonyl chloride, fluoro-2-nitro-4-azidobenzene, sulfonic esters, N-sulfonyl ureas, thiosulfato-S-alkyl ester, N-methylol urea, N,N'-dimethylol glyoxal monoureine, terephthal dialdehyde, mesithylene trialdehyde, isothiuronium groups, triacyl formal.

The above listed synthetic polymers and biopolymers as well as the polymer derivatives prepared from them can be used according to the invention to embody HS I with the above listed cross-linkers respectively the functional groups of cross-linkers or with the methods for surface modification of polymers. Analogous to that, HS I can be used with the above listed cross-linking molecules, respectively the functional groups of cross-linkers and with the methods of surface modification to modify HS I for the anchoring to polymers, according to the invention. The covalent linking of HS I to polymer substrates can occur either with a cross-linking length of "0" (self cross-linking or cross-linking under participation of merely functional groups of the polymer substrate and of HS I or with a cross-linking length of greater than "0" by using hydrophilic, hydrophobic, amphiphilic, charged, uncharged, flexible or bulky, spacers in the order of magnitude of 0.2–9 nm.

The embodiment of HS I to polymers or polymer derivatives can also occur through 1. salt-like bindings to positively charged groups of polymers, e.g. quarternary ammonium groups and phosphonium groups 2. chelation according to known methods for the preparation of chelate bonds between functional groups of macromolecules and metals
3. hydrophobic interactions by way of derivating of HS I and/or polymer surfaces with saturated and/or unsaturated long-chain hydrocarbons, whose length consists of 8–30 methylene groups, containing the known functional groups, or with cyclic, saturated or unsaturated hydrocarbons, whose carbon number ranges from 6 to 50.

In addition to that the embodiment of HS I can occur through adsorption, enclosure into polymer networks, encapsulation or physical mixture according to the methods of plastic processing.

The hemo compatible substrates are used according to the invention in the form of fibres, hollow fibres, membranes, organ spare parts, canulas, syringes, tubes, blood containers or other forms and the used or synthesized polymers are chosen according to their physical, mechanical-technological, and chemical features, needed here.

EXAMPLES

The following examples are supplied to explain the presented invention. First of all the production of HS I for the invented embodiment to polymer substrates is described. Then the covalent embodiment to polymer substrates is described for a few selected examples, where one class of polymers is mostly used for better comprehension.

EXAMPLE 1

Production of HS I from cultivated bovine aorta-endothelial cells for embodiment to polymer substrates Aortae of cattle are taken from freshly slaughtered animals. They are freed from fatty tissue and the aorta intercostales are ligated with clips. Then the aortae are cleaned with $3 \times 50$ ml sterile PBS and on one end ligated with a clip. A sterile solution of 0.1% bovine Pankreas Trypsine (Boehringer Mannheim) in 1 mM EDTA/PBS is filled into the aorta from above, and the second end is ligated. The aortae are then incubated in a water bath at 37° C. for 7.5 min.

One of the final aorta-ligatures is removed and the liquid is removed with a sterile pipette. The cells, suspended in the solution, are centrifuged at $800 \times g$ and 37° C., and suspended in sterile Dulbecco's modified essential medium (DMEM) 10% fetal cattle serum in the presence of 10,000 U penicillin and 10,000 U streptomycine (endothelial cell medium) at 37° C.

A sterile 75 cm$^2$ tissue culture flask is incubated for 1 h at 37° C. with 20 ml endothelial cell medium. The centrifuged cells, suspended in 1 ml endothelial cell medium are added to this flask. It is then stored in an incubator at 37° C. in an atmosphere of 5% $CO_2$ and saturated water vapour to culture the cells.

The cells are characterized morphologically and by staining with antibovine Factor VIIIa antibodies (Dianova, Hamburg).

The cells are cultured to confluence, washed with sterile PBS, removed from the base through incubation with 2 ml 0.1% trypsine in 1 ml EDTA/PBS for 3 min at 37° C., mixed with 5 ml endothelial cell medium, centrifuged at $800 \times g$, resuspended in 9 ml endothelial cell medium, and 3 ml of this suspension are sowed in three new 75 cm, tissue culture flasks as described above.

For mass culture, the cells are sowed in cylindrical bottles in the same manner as is described for the culturing in the 75 cm, flasks About 10$^9$ cells are taken for one HS I preparation. To prepare the HS I preparation, the cells are removed from the base with 1 ml EDTA in PBS, homogenized through supersonics treatment for three times à 30 s at 0° C., each time interrupted for 1 min, centrifuged at $10,000 \times g$ and the supernatant is adjusted to 2% SDS. This solution (ca. 5 ml) is put on a Sepharose CL-6B column ($5 \times 100$ cm). It is eluted with 0.1% SDS, 0.1M Tris/HCl, 1 mM PMSF, 1 mM EDTA pH 7.5. Fractions of 20 ml are taken at a flow rate of 100 ml/h.

The void of the column chromatography (fractions 35–50) are precipitated in 80% ethanol, centrifuged at $10,000 \times g$, dried in vacuum, dissolved in 50 ml 7M urea, 0.1% CHAPS (3-(3-cholamidopropyl)-dimethyl ammonio)-1-propane sulfonate). 0.1M Tris/HCl, 1 mM PMSF, 1 mM EDTA pH 7.3 (buffer solution) and put on a DEAE-cellulose column ($2.5 \times 5$ cm). The column is equilibrated with 100 ml of the buffer solution and then eluted with a linear gradient of 0–1M NaCl on basis of the buffer solution ($250 + 250$ ml). The fractions, which elute between 0.45–0.6M NaCl, are collected, precipitated in 80% ethanol, centrifuged at $10,000 \times g$ and dried in vacuo.

The substance is dissolved in 12.8 ml 0.1M Tris/HCl, 4M guanidinium hydrochloride and cesium chloride of the density 1.4 g/ml and centrifuged in a SW 40 rotor (Beckmann) at 35 000 Upm for 60 h. The centrifuge tube is punctuated on the ground and fractions of 1 ml are collected. The fractions of a density greater than 1.4 g/ml are collected, precipitated in 80% ethanol, centrifuged a $10,000 \times g$ and dried in vacuo.

The substance is dissolved in 2 ml 0.1M Tris/HCl, 1 mM PMSF, 1 mM EDTA pH 7.5 and incubated with 1 U Chondroitinase ABC and 100 U RNAse (Boehringer Mannheim) for 1 h at 37° C. Then the substance is chromatographed on Sepharose CL-6B, as described above. The yield is about 14 mg/10$^9$ on average endothelial cells.

EXAMPLE 2

Extraction of HS I polysaccharide from conditioned human umbilical endothelial cell medium The umbilical veins from fresh human umbilical cords are washed with sterile PBS, and are then perfused with a sterile solution of 10,000 U collagenase (Boehringer Mannheim) in cord-buffer for 5 minutes at 37° C. The cells are centrifuged at 37° C. and $800 \times g$ for 5 minutes.

Human sera are extracted from human blood through coagulation and centrifugation at $2,000 \times g$. They are not allowed to show any pathological values on a SMA-12 profile.

Bovine growth factor is purified from 10 cattle hypothalami of freshly slaughtered animals through homogenization and extraction with acetone/chloroform 2:1. The residue, which is insoluble in the degreasing agent, is used in amounts of 15–50 mg/1 culture medium.

Human fibronectin is extracted from human plasma. For this, 10 g gelatin (Sigma) is dissolved in 50 ml 0.2M NaAc at 65° C. 200 ml Sepharose CL-2B is caused to react with 10 g bromocyanogen at a pH of 10.5 for 10 min. The gel is then washed with 10 l 0.2M NaAc and shaken together with the gelatin solution for 24 h at 4° C. After the addition of 5 ml aminoethanol, the solution is again shaken for 7 h. The gel is washed with 4M guanidinium chloride and then with PBS (each 1 l). 1 l human plasma is shaken together with the gel for 24 h at 4° C. Then it is washed with 5 l PBS on a filter and eluted with 200 ml 1M NaCl. The eluate is dialyzed against 3×5 l PBS and sterilized by filtration on an 0.2 μm filter.

The human endothelial cells are suspended in 20 ml DMEM+10% human serum in the presence of 10,000 U penicillin, 10,000 U streptomycine and growth factor. A 75 cm, tissue culture flask is incubated with 2 ml fibronectin solution at room temperature for 3 h. The solution is removed, the flask washed with PBS and the cells are added. The flask is put into an incubator for culturing of the cells (s. above).

Passage and mass cultivation in cylindical bottles is made with the same media and culture vessel preparations, as well as cell culture techniques, as described.

The collected conditioned media (about 25 l) are adjusted with 10M NaOH to 0.5M NaOH and are incubated for 12 h at 4° C. The medium is then adjusted with 10M HCl to pH 1.5 at 4° C. and centrifuged at 10,000×g. The supernatant is neutralized with 10M NaOH and ultrafiltrated on Amicon PM 10 membranes up to a volume of 100 ml. The solution is adjusted to 80% ethanol, allowed to stand for 12 h at 4° C. and centrifuged at 10,000×g. The precipitate is solubilized in PBS, incubated with 10 U Chondroitinase ABC at 56° C. for 1 h and put on a Dowex 1×2 column (20 ml gel). The column is washed with 20 ml 1M NaCl and 4M NaCl each. The 4M NaCl eluate is dialized against water and lyophilized. The yield is about 1.2 mg.

EXAMPLE 3

Coupling of HS I to silicone 1 g silicone with free OH groups is mixed with 18 ml distilled water and 2 ml γ-aminopropyl triethoxysilane (10% v/v) and the pH value is adjusted between pH 3 and 4 with 6M HCl. After the pH adjustment, the solution is heated to 75° C. for 2 h, washed and dried. 1 g amino group containing silicone is mixed with 2.5% aqueous glutar dialdehyde solution in 0.05M Na phosphate buffer and adjusted to pH 7.0, reaction time 60 min. The activated silicone is caused to react with a 1% solution of HS I by stirring for 2–4 h. Washing is performed with 6M urea.

EXAMPLE 4

Isothiocyanate coupling reaction of HS I to silicone 1 g amino group containing silicone is caused to react with a 10% solution of thiophosgene in chloroform (v/v). The reaction mixture is refluxed for at least 4 h, better 12–15 h. It is washed with dry chloroform and dried in vacuo. An aqueous 1% HS I solution is slowly added to the isocyanate silicone (50–100 mg HS I/g silicone). The pH value is adjusted to 8.5 and the reaction takes place for 2 h, then it is washed with a 6M urea solution.

EXAMPLE 5

Carbodiimide coupling of HS I to amino group containing silicone 50 ml 0.03M phosphoric acid, pH 4.0, are added to 1 g amino group containing silicone. Then 100–200 mg water soluble carbodiimide and 50–100 mg HS I are added to the mixture and left for reaction for 24 h. It is washed in the same way as described above.

EXAMPLE 6

Triazine coupling of HS I to amino group containing silicone 10 ml benzene that contains 0.2 ml triethylamine and 0.3 g 1,3-dichloro-5-methoxytriazine are added to 1 g amino group containing silicone. The reaction mixture is held at 45–55° C. for 2–4 h. The coupling with HS I (50–100 mg) takes place in 0.05M phosphate buffer at pH 8 at 4° C. over night. It is washed in the same way as described above.

EXAMPLE 7

Immobilization of HS I on glutar dialdehyde 0.1 to 10 ml dilute glutar dialdehyde solutions (0.1–5%) are added to 1 g dispersed or impregnated amino group containing polymer and 10 mg HS I and caused to react at pH 7.4 for 0.5–2 min. Then it is washed with cold water directly.

EXAMPLE 8

Thermic and photochemical immobilization of HS I on polymers 1 g fluoro-2-nitro-4-azidobenzene is caused to react with 10 g HS I in the dark at 50° C. and maximum pH 10.5 in 0.05M sodiumborate buffer for 16–64 h. The reaction product is filtered and washed with 95% ethanol. The photo immobilization to polymers occurs in some hours at 200–300 Watt with a mercury vapour lamp. Then it is washed as described above.

EXAMPLE 9

Embodiment of HS I through oxirane groups and hydroxyl and amino group containing polymers 0 g washed 2% agarose gel is suspended in 5 ml 2.5M NaOH solution. 20 g sodium borohydride is added and then 1,4-butandiol diglycid ether is added dropwise under strong stirring. The reaction lasts 6 h at room temperature. Then 50 ml acetone are added and afterwards water. The oxirane gel is suspended in 25 ml 0.5M sodiumbicarbonate and 50 mg HS I are added. The reaction lasts 5 h. The product is washed as described above.

EXAMPLE 10

Azo coupling of HS I through arylamine groups to polymers 1 g amino group containing silicone is suspended in 25–30 ml chloroform that contains 5% triethylamine (v/v) and 1 g p-nitrobenzoyl chloride. The reaction mixture is refluxed for at least 4 h. It is washed with dry chloroform and refluxed in a 5% sodium dithionit solution. The azo coupling occurs with 1 g arylamine silicone by adding 20 ml 2N HCl in an ice bath. 100 mg solid sodium nitrite is added and diazotated for 30 min. Then it is washed with ice water. 100 mg HS I are dissolved in 0.05M sodium phosphate a pH 8.5 and 1 g diazotated polymer is added. The coupling occurs between 2–18 h. The product is washed as described above.

EXAMPLE 11

Preparation of polymer bound HS I through copolymerization with alkylation and acylation monomers 3,4-epoxybutene, acrylic acid-2,3-epoxypropyl ester, acrylic acid-2,3-thioglycidyl ester, 1-allyloxy-3-(N-ethylenimine)-2propanol, acrylic acid-0-succinimide ester or acrylic acid chloride, maleic anhydride, chloromaleic anhydride, maleinazide or bromopropene are caused to react with HS I in equimolar amounts and are then polymerized or copolymerized according to the usual methods.

We claim:

1. A process for the preparation of a non-thrombogenic substance comprising
    binding HS I to a polymer substrate having a surface, said polymer being selected from the group consisting of a biopolymer, a synthetic polymer, a copolymer thereof, and a derivative thereof;
    said binding of HS I to said polymer is by means selected from the group consisting of salt-bridges, covalent bonds, ionic bonds, hydrophobic interactions, hydrogen bonds, Van der Waals forces, adsorption, microencapsulation, and network enclosure; and
    wherein HS I is a specific endothelial cell surface proteo polysaccharide produced by the cell and having three to four polysaccharide side-chains which have a molecular weight of about 35,000 each, and a central protein core of a molecular weight of about 55,000, said polysaccharide sidechains having no interaction with blood coagulation factors and no other biological activity as observed for a substance selected from the group consisting of glycosaminoglycans, heparins, and heparan sulfates.

2. A process according to claim 1 comprising binding said HS I to said polymer substrate by said protein core of the HS I.

3. A process according to claim 1, comprising covalently binding said HS I to said polymer.

4. A process according to claim 1, comprising activating said HS I and then binding it to said polymer substrate,
    or activating said polymer substrate and then binding said HS I to the polymer substrate, or activating said HS I and activating said polymer substrate and then binding HS I to the polymer substrate.

5. A process according to claim 1, wherein
    binding of said HS I to said polymer occurs directly by participation of functional groups of the polymer substrate and HS I or with bifunctional molecules which bind to HS I and to the polymer substrate thereby linking said HS I to said polymer and which have a distance between the HS I binding site and the polymer binding site within the bifunctional molecule ranging from 0.2 to 5 nm.

6. A process according to claim 1, wherein said polymer has a backbone; and
    said ionic bonds occur by direct involvement of charged groups of said HS I and charged groups of said polymer, or by participation of charged substances which form ionic bonds to the polymer and to HS I thereby linking HS I to the polymer and which have a distance between the HS I binding site and the polymer binding site within the charged substance ranging from 0.15 to 200 nm.

7. A process according to claim 1, wherein
    said polymer has a backbone and carries covalently linked side chains of a length between 0.15 to 200 nm with charged groups and wherein said ionic bonds occur by direct interaction of charged groups of said HS I and charged groups of the polymer side chains.

8. A process according to claim 1, comprising first binding HS I to the charged groups,
    of a hydrophobic chain molecule of a length between 0.15 and 200 nm and then binding the so modified HS I to hydrophobic parts of the polymer substrate.

9. A process according to claim 1, comprising
    binding said HS I to a polymer substrate by ionic bonds, hydrophobic interactions, hydrogen bonds, and Van der Waals forces and then covalently binding HS I to the polymer by participation of functional groups of HS I and the polymer.

10. A process according to claim 1, comprising:
    covalently binding HS I to vinyl monomer to form HS I - vinyl monomer and then copolymerizing said HS I - vinyl monomer together with vinyl monomer.

11. A process according to claim 1, wherein the concentration of HS I is of 1 $\mu$g–1000 $\mu$g per square centimeter polymer surface.

12. A process for the preparation of a non-thrombogenic substance comprising:
    binding HS I to a polymer substrate having a surface, said polymer being selected from the group consisting of a bipolymer, a synthetic polymer, a copolymer thereof, and a derivative thereof;
    said binding being about 0.01–100 $\mu$g HS I per square centimeter covalently to said polymer surface and wherein between 1 and 80 covalent binding places or cross-linking bridges between HS I and said polymer exist; and
    wherein HS I is a specific endothelial cell surface proteo polysaccharide produced by the cell and having three to four polysaccharide side-chains which have a molecular weight of about 35,000 each, and a central protein core of a molecular weight of about 55,000, said polysaccharide sidechains having no interaction with blood coagulation factors and no other biological activity as observed for a substance selected from the group consisting of glycosaminoglycans, heparins, and heparan sulfates.

13. A process for the preparation of a non-thrombogenic substance comprising:
    binding HS I to a polymer substrate having a surface, said polymer being selected from the group consisting of a biopolymer, a synthetic polymer, a copolymer thereof, and a derivative thereof;
    wherein HS I is a specific endothelial cell surface proteo polysaccharide produced by the cell and having three to four polysaccharide side-chains which have a molecular weight of about 35,000 each, and a central protein core of a molecular weight of about 55,000, said polysaccharide sidechains having no interaction with blood coagulation factors and no other biological activity as observed for a substance selected from the group consisting of glycosaminoglycans, heparins, and heparan sulfates; and wherein said binding comprises binding said HS I polysaccharide chain covalently to the polymer substrate.

14. In a process for providing a substrate having a surface for being contacted by blood, the improvement which comprises utilizing the non-thrombogenic substance as said substrate, which is prepared by a process for the preparation of a non-thrombogenic substance comprising:

binding HS I to a polymer substrate having a surface, said polymer being selected from the group consisting of a biopolymer, a synthetic polymer, a copolymer thereof, and a derivative thereof;

said binding of HS I to said polymer by means is selected from the group consisting of salt-bridges, covalent bonds, ionic bonds, hydrophobic interactions, hydrogen bonds, Van der Waals forces, adsorption, microencapsulation, and network enclosure; and wherein HS I is a specific endothelial cell surface proteo polysaccharide produced by the cell and having three to four polysaccharide side-chains which have a molecular weight of about 35,000 each, and a central protein core of a molecular weight of about 55,000, said polysaccharide side-chains having no interaction with blood coagulation factors and no other biological activity as observed for a substance selected from the group consisting of glycosaminoglycans, heparins, and heparan sulfates.

15. The process according to claim 14, wherein the concentration of HS I is of 1 μg–1000 μg per square centimeter polymer surface.

* * * * *